United States Patent
Hu et al.

(10) Patent No.: US 6,342,642 B1
(45) Date of Patent: Jan. 29, 2002

(54) 1,4-DIARYL-2-FLUORO-1-BUTEN-3-OL COMPOUNDS AND THEIR USE IN THE PREPARATION OF 1,4-DIARYL-2-FLUORO-1, 3-BUTADIENE AND 1,4-DIARYL-2-FLUORO-2-BUTENE COMPOUNDS

(75) Inventors: Yulin Hu, Plainsboro, NJ (US); David Allen Hunt, Clifton Park, NY (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/856,229

(22) PCT Filed: Nov. 9, 1999

(86) PCT No.: PCT/US99/26434

§ 371 Date: Aug. 13, 2001

§ 102(e) Date: Aug. 13, 2001

(87) PCT Pub. No.: WO00/29362

PCT Pub. Date: May 25, 2000

(51) Int. Cl.$^7$ .............................................. C07C 43/215
(52) U.S. Cl. .................. 568/637; 546/290; 546/343; 568/633; 568/634; 568/639; 568/645; 568/647; 568/807; 568/808; 568/809; 570/129
(58) Field of Search ................... 568/637, 639, 568/807, 808, 809, 633, 634, 645, 647; 546/343, 290; 570/129

(56) References Cited

U.S. PATENT DOCUMENTS 5,849,958 A  * 12/1998  Barnes
5,998,673 A  * 12/1999  Barnes

FOREIGN PATENT DOCUMENTS

EP         0811593 A      12/1997
EP         0811596 A      12/1997

OTHER PUBLICATIONS

B. M. Mikhailov, et al. Bull. of The Academy of Sciences of the USSR, Div. of Chem. Sc., No. 7, Jul. 1956, pp. 1489–1492.

* cited by examiner

*Primary Examiner*—Michael L. Shippen
(74) *Attorney, Agent, or Firm*—Barbara V. Maurer

(57) ABSTRACT

The present invention provides novel 1,4-diaryl-2-fluoro-1-buten-3-ol compounds of the structural formula I

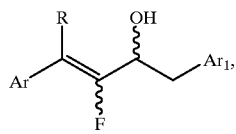

(I)

a method for the preparation of those formula I compounds, and the use of those formula I compounds in the preparation of 1,4-diaryl-2-fluoro-1,3-butadiene compounds of formula II and 1,4-diaryl-2-fluoro-2-butene compounds of formula III

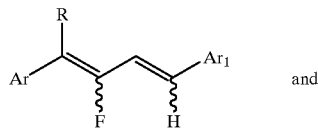

(II)

and

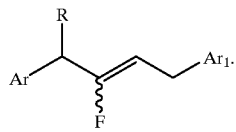

(III)

32 Claims, No Drawings

1,4-DIARYL-2-FLUORO-1-BUTEN-3-OL COMPOUNDS AND THEIR USE IN THE PREPARATION OF 1,4-DIARYL-2-FLUORO-1,3-BUTADIENE AND 1,4-DIARYL-2-FLUORO-2-BUTENE COMPOUNDS

BACKGROUND OF THE INVENTION 1,4-Diaryl-2-fluoro-1,3-butadiene compounds, methods for their preparation, and their use as intermediates in the preparation of 1,4-diaryl-2-fluoro-2-butene insecticidal and acaricidal agents are described in EP 811593-A1. The methods described in EP 811593-A1 for the preparation of 1,4-diaryl-2-fluoro-1,3-butadiene compounds require the use of phosphonium halide compounds. However, these methods are not entirely satisfactory because the required phosphonium halide compounds are relatively expensive and produce undesirable by-products which are difficult to remove from the 1,4-diaryl-2-fluoro-1,3-butadiene compounds. Accordingly, a need exists in the art for an improved process for the preparation of 1,4-diaryl-2-fluoro-1,3-butadiene compounds which avoids the use of phosphonium halide compounds.

It is, therefore, an object of the present invention to provide new compounds which are useful in the preparation of 1,4-diaryl-2-fluoro-1,3-butadiene compounds.

It is also an object of the present invention to provide an improved process for the preparation of 1,4-diaryl-2-fluoro-1,3-butadiene compounds which avoids the use of phosphonium halide compounds.

It is a further object of this invention to provide an improved process for the preparation of 1,4-diaryl-2-fluoro-2-butene compounds.

Other objects and advantages of the present invention will be apparent to those skilled in the art from the description below and the appended claims.

SUMMARY OF THE INVENTION

The present invention provides 1,4-diaryl-2-fluoro-1-buten-3-ol compounds of the structural formula I

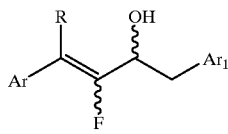

(I)

wherein
R is hydrogen, $C_1$–$C_4$alkyl, $C_1$–$C_4$haloalkyl, $C_3$–$C_6$cycloalkyl or $C_3$–$C_6$halocycloalkyl;
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups,
  1- or 2-naphthyl optionally substituted with any combination of from one to three halogen, $C_1$–$C_4$alkyl, $C_1$–$C_4$haloalkyl $C_1$–$C_4$alkoxy or $C_1$–$C_4$haloalkoxy groups, or
  a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and
$Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
  phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
  a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups.

The present invention also provides a new process for the preparation of 1,4-diaryl-2-fluoro-1,3-butadiene compounds of the structural formula II

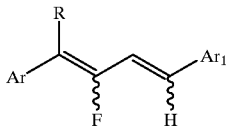

(II)

wherein
R is hydrogen, $C_1$–$C_4$alkyl, $C_1$–$C_4$haloalkyl, $C_3$–$C_6$cycloalkyl or $C_3$–$C_6$halocycloalkyl;
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups,
  1- or 2-naphthyl optionally substituted with any combination of from one to three halogen, $C_1$–$C_4$alkyl, $C_1$–$C_4$haloalkyl $C_1$–$C_4$alkoxy or $C_1$–$C_4$haloalkoxy groups, or
  a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and
$Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
  phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, which process comprises reacting a 1,4-diaryl-2-fluoro-1-buten-3-ol compound of the structural formula I

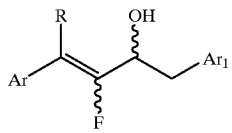

(I)

wherein Ar, $Ar_1$ and R are as hereinbefore defined with a sulfonyl chloride or sulfonic acid anhydride compound and a base.

The present invention further provides a new process for the preparation of 1,4-diaryl-2-fluoro-2-butene compounds having the structural formula III

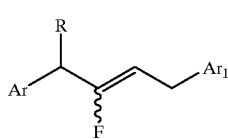

(III)

wherein

R is hydrogen, $C_1$–$C_4$alkyl, $C_1$–$C_4$haloalkyl, $C_3$–$C_6$cycloalkyl or $C_3$–$C_6$halocycloalkyl;

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, $C_1$–$C_4$alkyl, $C_1$–$C_4$haloalkyl $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and $Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups, phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, which process comprises:

(a) reacting a 1,4-diaryl-2-fluoro-1-buten-3-ol compound of the structural formula I

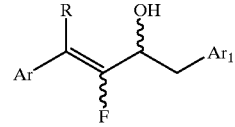

(I)

wherein Ar, $Ar_1$ and R are as described above with a sulfonyl chloride or sulfonic acid anhydride compound and a base to form a 1,4-diaryl-2-fluoro-1,3-butadiene compound of the structural formula II

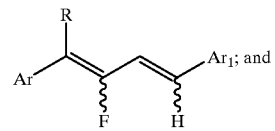

(II)

(b) reacting the 1,4-diaryl-2-fluoro-1,3-butadiene compound with: (1) an alkaline earth metal in the presence of a protic solvent, or (2) an alkali metal in the presence of an aprotic solvent.

DETAILED DESCRIPTION OF THE INVENTION

The present invention provides 1,4-diaryl-2-fluoro-1-buten-3-ol compounds having the structural formula I

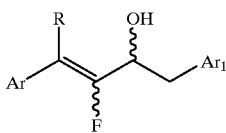
(I)

wherein Ar, Ar$_1$ and R are as described hereinbefore defined.

Preferred formula I compounds of this invention are those wherein

R is C$_1$–C$_4$alkyl, C$_1$–C$_4$haloalkyl, C$_3$–C$_6$cycloalkyl or C$_3$–C$_6$halocycloalkyl;

Ar is phenyl optionally substituted with any combination of from one to three halogen, C$_1$–C$_4$alkyl, C$_1$–C$_4$haloalkyl, C$_1$–C$_4$alkoxy or C$_1$–C$_4$ haloalkoxy groups; and Ar$_1$ is 3-phenoxyphenyl optionally substituted with any combination of from one to six halogen, C$_1$–C$_4$alkyl, C$_1$–C$_4$haloalkyl, C$_1$–C$_4$alkoxy or C$_1$–C$_4$haloalkoxy groups, 3-biphenyl optionally substituted with any combination of from one to five halogen, C$_1$–C$_4$alkyl, C$_1$–C$_4$haloalkyl, C$_1$–C$_4$alkoxy or C$_1$–C$_4$haloalkoxy groups, or 3-benzylphenyl optionally substituted with any combination of from one to five halogen, C$_1$–C$_4$alkyl, C$_1$–C$_4$haloalkyl, C$_1$–C$_4$alkoxy or C$_1$–C$_4$haloalkoxy groups.

More preferred 1,4-diaryl-2-fluoro-1-buten-3-ol compounds of this invention are those wherein R is isopropyl or cyclopropyl;

Ar is phenyl optionally substituted with any combination of from one to three halogen, C$_1$–C$_4$alkyl, C$_1$–C$_4$haloalkyl, C$_1$–C$_4$alkoxy or C$_1$–C$_4$haloalkoxy groups; and Ar$_1$ is 3-phenoxyphenyl optionally substituted with any combination of from one to six halogen, C$_1$–C$_4$alkyl, C$_1$–C$_4$haloalkyl, C$_1$–C$_4$alkoxy or C$_1$–C$_4$haloalkoxy groups.

1-(p-Chlorophenyl)-1-cyclopropyl-2-fluoro-4-(4-fluoro-3-phenoxyphenyl)-1-buten-3-ol and 1-(α,α,α-trifluoro-p-tolyl)-1-cyclopropyl-2-fluoro-4-(4-fluoro-3-phenoxyphenyl)-1-buten-3-ol are especially useful for the preparation of highly active insecticidal and acaricidal agents of formula III.

In formulas I, II and III above, the 5- and 6-membered heteroaromatic ring may suitably be a ring containing one to four heteroatoms selected from N, O and S, wherein the heteroatoms may be the same or different, e.g. the rings include, but are not limited to, pyridyl, pyrazolyl, imidazolyl, triazolyl, isoxazolyl, tetrazolyl, pyrazinyl, pyridazinyl, triazinyl, furanyl, thienyl and thiazolyl rings each optionally substituted as described in formulas I, II and III above.

Exemplary of "halogen" hereinabove are fluorine, chlorine, bromine and iodine. The terms "C$_1$–C$_4$haloalkyl", "C$_3$–C$_6$halocycloalkyl" and "C$_1$–C$_4$haloalkoxy" are defined as a C$_1$–C$_4$alkyl group, a C$_3$–C$_6$cycloalkyl group and a C$_1$–C$_4$alkoxy group substituted with one or more halogen atoms, respectively, wherein the halogen atoms may be the same or different.

When used herein as a group or part of a group, the term "alkyl" includes straight or branched chain alkyl groups such as methyl, ethyl, n-propyl, isopropyl, n-butyl, isobutyl, s-butyl and t-butyl. When used herein as a group or part of a group, the term "cycloalkyl" includes cyclopropyl, cyclobutyl, cyclopentyl and cyclohexyl.

Groups containing two or more rings, such as phenoxyphenyl, phenoxypyridyl, biphenyl and benzylphenyl, which may be substituted, may be substituted on either ring unless otherwise specified herein.

In a preferred embodiment of the present invention, the 1,4-diaryl-2-fluoro-1,3-butadiene compounds of formula II are prepared by reacting a 1,4-diaryl-2-fluoro-1-buten-3-ol compound of formula I with a sulfonyl chloride or sulfonic acid anhydride compound and a base, preferably at a temperature ranging from about –78° C. to 120° C., more preferably from about 20° C. to 80° C., in the presence of a solvent.

In another preferred embodiment of the present invention, the 1,4-diaryl-2-fluoro-2-butene compounds of formula III are prepared by reacting a 1,4-diaryl-2-fluoro-1-buten-3-ol compound of formula I with a sulfonyl chloride or sulfonic acid anhydride compound and a base, preferably at a temperature ranging from about –78° C. to 120° C., more preferably from about 20° C. to 80° C., in the presence of a solvent to form a 1,4-diaryl-2-fluoro-1,3-butadiene compound of formula II, and reacting the formula II butadiene compound with an alkaline earth metal in the presence of a protic solvent.

Advantageously, the present invention provides a process for the preparation of 1,4-diaryl-2-fluoro-1,3-butadiene compounds which avoids the use of phosphonium halide compounds.

The product formula II and III compounds may be isolated by diluting the reaction mixture with water and extracting the product with a suitable extraction solvent. In the isolation procedure, conventional extraction solvents such as diethyl ether, ethyl acetate, toluene, methylene chloride, and the like, and mixtures thereof may be utilized.

Sulfonyl chloride compounds suitable for use in the present invention include, but are not limited to, unsubstituted and substituted phenylsulfonyl chlorides such as p-toluenesulfonyl chloride and the like, C$_1$–C$_6$alkylsulfonyl chlorides such as methanesulfonyl chloride and the like, and C$_1$–C$_6$haloalkylsulfonyl chlorides such as trifluoromethanesulfonyl chloride and the like. Sulfonic acid anhydrides suitable for use in this invention include, but are not limited to, unsubstituted and substituted phenylsulfonic acid anhydrides such as p-toluenesulfonic acid anhydride and the like, C$_1$–C$_6$alkylsulfonic acid anhydrides such as methanesulfonic acid anhydride and the like, and C$_1$–C$_6$haloalkylsulfonic acid anhydrides such as trifluoromethanesulfonic acid anhydride and the like. Bases suitable for use in the present invention include, but are not limited to, alkali metal hydrides such as sodium hydride, potassium hydride, lithium hydride and the like, alkaline earth metal hydrides such as calcium hydride and the like, alkali metal C$_1$–C$_6$alkoxides such as sodium methoxide, potassium t-butoxide and the like, C$_1$–C$_6$alkyllithiums such as n-butyllithium, sec-butyllithium, methyllithium and the like, and lithium dialkylamides such as lithium diisopropylamide, lithium isopropylcyclohexylamide and the like. Preferred bases include alkali metal hydrides.

Solvents suitable for use in the preparation of the formula II and III compounds of this invention include, but are not limited to, ethers such as tetrahydrofuran, dioxane, pyran, diethyl ether, 1,2-dimethoxyethane and the like; carboxylic acid amides such as N,N-dimethylformamide, N,N-dimethylacetamide and the like; dialkyl sulfoxides such as dimethyl sulfoxide and the like; nitrites such as acetonitrile, propionitrile and the like; aromatic hydrocarbons such as toluene, benzene, xylenes, mesitylene and the like; and halogenated aromatic hydrocarbons such as chlorobenzene, fluorobenzene and the like; and mixtures thereof. Preferred solvents for use in the preparation of the formula II and III compounds include ethers.

Protic solvents suitable for use in this invention include, but are not limited to, $C_1$–$C_6$alcohols such as methanol, ethanol and the like. Preferred protic solvents include methanol and ethanol. Aprotic solvents include, but are not limited to, ammonia; and ethers such as diethyl ether, tetrahydrofuran, dioxane, 1,2-dimethoxyethane and the like.

Alkaline earth metals suitable for use in the preparation of the formula III compounds include, but are not limited to, magnesium and calcium with magnesium being preferred. Alkali metals include, but are not limited to, lithium, sodium and potassium.

Preferred formula II and III compounds which may be prepared by the processes of this invention are those wherein R is $C_1$–$C_4$alkyl, $C_1$–$C_4$haloalkyl, $C_3$–$C_6$cycloalkyl or $C_3$–$C_6$halocycloalkyl;

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups, 3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or 3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

More preferred 1,4-diaryl-2-fluoro-1,3-butadiene and 1,4-diaryl-2-fluoro-2-butene compounds which may be prepared by the processes of this invention are those wherein R is isopropyl or cyclopropyl;

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

The present invention is especially useful for the preparation of 1-(p-chlorophenyl)-1-cyclopropyl-2-fluoro-4-(4-fluoro-3-phenoxyphenyl)-1,3-butadiene;

1-(α,α,α-trifluoro-p-tolyl)-1-cyclopropyl-2-fluoro-4-(4-fluoro-3-phenoxyphenyl)-1,3-butadiene;

1-[1-(α,α,α-trifluoro-p-tolyl)-2-fluoro-4-(4-fluoro-3-phenoxyphenyl)-2-butenyl]cyclopropane; and 1-[1-(p-chlorophenyl)-2-fluoro-4-(4-fluoro-3-phenoxyphenyl)-2-butenyl]cyclopropane.

The present invention further provides a process for the preparation of 1,4-diaryl-2-fluoro-1-buten-3-ol compounds of formula I which process comprises:

(a) reacting an arylmethanebromide compound of the structural formula IV

wherein $Ar_1$ is as described hereinabove with a lithium $C_1$–$C_6$alkyltellurolate compound to form an intermediate compound of the structural formula V

(b) reacting the formula V intermediate compound with a $C_1$–$C_6$alkyllithium compound to form an intermediate compound of the structural formula VI

(c) reacting the formula VI intermediate compound with a 3-aryl-2-fluoropropenal compound of the structural formula VII

wherein R and Ar are as hereinbefore defined.

In a preferred embodiment of the present invention, the 1,4-diaryl-2-fluoro-1-buten-3-ol compounds of formula I are prepared by reacting an arylmethanebromide compound of formula IV with a lithium $C_1$–$C_6$alkyltellurolate compound, preferably at a temperature ranging from about −78° C. to about 30° C., more preferably from about −78° C. to about 0° C., in the presence of a solvent to form an intermediate compound of formula V, reacting the formula V intermediate compound in situ with a $C_1$–$C_6$alkyllithium compound, preferably at a temperature ranging from about −78° C. to about 30° C., more preferably from about −78° C. to about 0° C., to form an intermediate compound having the structural formula VI, and reacting the formula VI intermediate compound in situ with a 3-aryl-2-fluoropropenal compound of formula VII, preferably at a temperature ranging from about −78° C. to about 30° C.

Lithium $C_1$–$C_6$alkyltellurolate compounds suitable for use in the present invention include, but are not limited to, lithium n-butyltellurolate, lithium sec-butyltellurolate, lithium t-butyltellurolate, lithium n-propyltellurolate and the like. $C_1$–$C_6$alkyllithium compounds suitable for use include, but are not limited to, n-butyllithium, sec-butyllithium, n-propyllithium, methyllithium and the like.

Solvents useful in the preparation of the formula I compounds of this invention include, but are not limited to, ethers such as diethyl ether, tetrahydrofuran, 1,2-dimethoxyethane and the like and mixtures thereof, with tetrahydrofuran being preferred.

In order to facilitate a further understanding of this invention, the following examples are presented primarily for the purpose of illustrating more specific details thereof. The scope of the invention should not be deemed limited by the examples but encompasses the entire subject matter defined in the claims.

EXAMPLE 1

Preparation of 1-(p-Chlorophenyl)-1-cyclopropyl-2-fluoro-4-(4-fluoro-3-phenoxyphenyl)-1-buten-3-ol

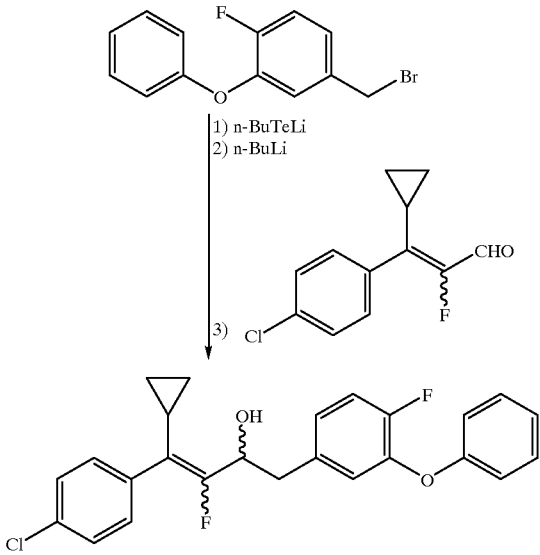

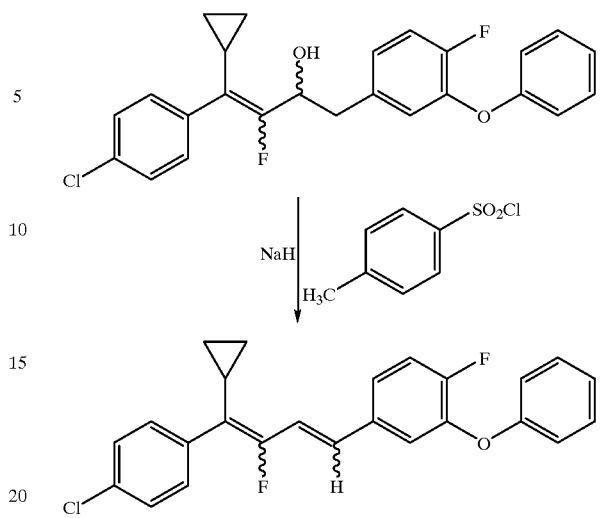

A solution of lithium n-butyltellurolate (10.5 mmol, n-BuTeLi), generated in situ from n-butyllithium (4.2 ml of 2.5 M solution in hexane, 10.5 mmol) and Te powder (1.34 g, 10.5 mmol) in tetrahydrofuran (10 ml) at 0° C., is treated with a solution of 3-phenoxy-4-fluorobenzyl bromide (2.81 g, 10 mmol) in tetrahydrofuran (10 ml) at 0° C., stirred for 30 minutes, cooled to −78° C., treated with a solution of n-butyllithium (4.2 ml of 2.5 M solution in hexane, 10.5 mmol), stirred for 30 minutes at −78° C., treated with a solution of p-chloro-β-cyclopropyl-α-fluorocinnamaldehyde (2.24 g, 10 mmol) in tetrahydrofuran (5 ml), warmed to room temperature with stirring for 3 hours, quenched with 2 N hydrochloric acid, and extracted with ethyl acetate. The combined organic extracts are washed with water, dried over anhydrous sodium sulfate, and concentrated in vacuo to obtain a residue. Flash chromatography of the residue on silica gel using a 1:4 ethyl acetate/hexanes solution gives the title product (3.5 g, 82% yield) which is identified by $^1$H, $^{19}$F and $^{13}$C NMR spectral analyses.

Following essentially the same procedure, but using p-(trifluoromethyl)-β-cyclopropyl-α-fluorocinnamaldehyde, 1-(α,α,α-trifluoro-p-tolyl)-1-cyclopropyl-2-fluoro-4-(4-fluoro-3-phenoxyphenyl)-1-buten-3-ol is obtained.

EXAMPLE 2

Preparation of 1-(p-Chlorophenyl)-1-cyclopropyl-2-fluoro-4-(4-fluoro-3-phenoxyphenyl)-1,3-butadiene A suspension of sodium hydride (6.3 mg, 0.26 mmol) in tetrahydrofuran (1 ml) is treated with a solution of 1-(p-chlorophenyl)-1-cyclopropyl-2-fluoro-4-(4-fluoro-3-phenoxyphenyl)-1-buten-3-ol (106.7 mg, 0.25 mmol) in tetrahydrofuran (1.5 ml), stirred at 50° C. for 10 minutes, cooled to room temperature, treated with a solution of p-toluenesulfonyl chloride (49.6 mg, 0.26 mmol) in tetrahydrofuran (1 ml), stirred at 60° C. for 1 hour, quenched with water, and extracted with ethyl acetate. The combined organic extracts are washed sequentially with water, saturated sodium hydrogen carbonate solution and water, dried over anhydrous sodium sulfate, and concentrated in vacuo to obtain a residue. Flash chromatography of the residue using silica gel and a 1:9 ethyl acetate/hexanes solution gives the title product (62 mg, 61% yield) which is identified by $^1$H, $^{19}$F and $^{13}$C NMR spectral analyses.

Following essentially the same procedure, but using 1-(α,α,α-trifluoro-p-tolyl)-1-cyclopropyl-2-fluoro-4-(4-fluoro-3-phenoxyphenyl)-1-buten-3-ol, 1-(α,α,α-trifluoro-p-tolyl)-1-cyclopropyl-2-fluoro-4-(4-fluoro-3-phenoxyphenyl)-1,3-butadiene is obtained.

What is claimed is:

1. A compound of the structural formula I

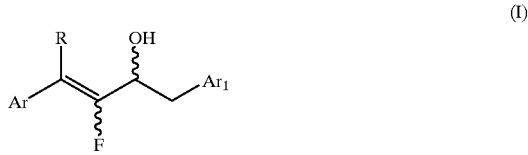

(I)

wherein
R is hydrogen, $C_1$–$C_4$alkyl, $C_1$–$C_4$haloalkyl, $C_3$–$C_6$cycloalkyl or $C_3$–$C_6$halocycloalkyl;
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups,
1- or 2-naphthyl optionally substituted with any combination of from one to three halogen, $C_1$–$C_4$alkyl, $C_1$–$C_4$haloalkyl $C_1$–$C_4$alkoxy or $C_1$–$C_4$haloalkoxy groups, or
a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and $Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups, phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups.

2. The compound according to claim 1 wherein

R is $C_1$–$C_4$alkyl, $C_1$–$C_4$haloalkyl, $C_3$–$C_6$cycloalkyl or $C_3$–$C_6$halocycloalkyl;

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups, 3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or 3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

3. The compound according to claim 2 wherein

R is isopropyl or cyclopropyl;

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

4. The compound according to claim 1 selected from the group consisting of 1-(p-chlorophenyl)-1-cyclopropyl-2-fluoro-4-(4-fluoro-3-phenoxyphenyl)-1-buten-3-ol and 1-(α,α,α-trifluoro-p-tolyl)-1-cyclopropyl-2-fluoro-4-(4-fluoro-3-phenoxyphenyl)-1-buten-3-ol.

5. A process for the preparation of a 1,4-diaryl-2-fluoro-1,3-butadiene compound of the structural formula II

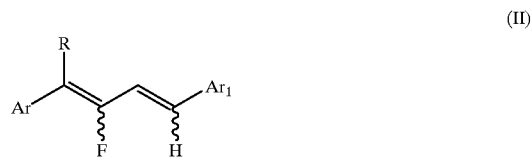

wherein

R is hydrogen, $C_1$–$C_4$alkyl, $C_1$–$C_4$haloalkyl, $C_3$–$C_6$cycloalkyl or $C_3$–$C_6$halocycloalkyl;

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, $C_1$–$C_4$alkyl, $C_1$–$C_4$haloalkyl $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and $Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups, phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, which process comprises reacting a 1,4-diaryl-2-fluoro-1-buten-3-ol compound of the structural formula I

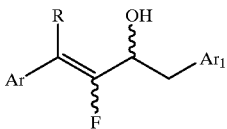

(I)

wherein Ar, Ar$_1$ and R are as hereinbefore defined with a sulfonyl chloride or sulfonic acid anhydride compound and a base.

6. The process according to claim 5 wherein the sulfonyl chloride is selected from the group consisting of phenylsulfonyl chloride, a substituted phenylsulfonyl chloride, a $C_1$–$C_6$alkylsulfonyl chloride and a $C_1$–$C_6$haloalkylsulfonyl chloride; and the sulfonic acid anhydride is selected from the group consisting of phenylsulfonic acid anhydride, a substituted phenylsulfonic acid anhydride, a $C_1$–$C_6$alkylsulfonic acid anhydride and a $C_1$–$C_6$haloalkylsulfonic acid anhydride.

7. The process according to claim 5 wherein the base is selected from the group consisting of an alkali metal hydride, an alkaline earth metal hydride, an alkali metal $C_1$–$C_6$alkoxide, a $C_1$–$C_6$alkyllithium and a lithium dialkylamide.

8. The process according to claim 7 wherein the base is an alkali metal hydride.

9. The process according to claim 5 wherein the 1,4-diaryl-2-fluoro-1-buten-3-ol compound is reacted with the sulfonyl chloride or sulfonic acid anhydride compound and the base in the presence of a solvent.

10. The process according to claim 9 wherein the solvent is selected from the group consisting of an ether, a carboxylic acid amide, a dialkyl sulfoxide, a nitrile, an aromatic hydrocarbon and a halogenated aromatic hydrocarbon and mixtures thereof.

11. The process according to claim 5 wherein the 1,4-diaryl-2-fluoro-1-buten-3-ol compound is reacted with the sulfonyl chloride or sulfonic acid anhydride compound and the base at a temperature ranging from about –78° C. to about 120° C.

12. The process according to claim 5 wherein
R is $C_1$–$C_4$alkyl, $C_1$–$C_4$haloalkyl, $C_3$–$C_6$cycloalkyl or $C_3$–$C_6$halocycloalkyl;
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and
Ar$_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or
3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

13. The process according to claim 12 wherein
R is isopropyl or cyclopropyl;
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and Ar$_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

14. The process according to claim 5 for the preparation of a compound selected from the group consisting of
1-(p-chlorophenyl)-1-cyclopropyl-2-fluoro-4-(4-fluoro-3-phenoxyphenyl)-1,3-butadiene and
1-(α,α,α-trifluoro-p-tolyl)-1-cyclopropyl-2-fluoro-4-(4-fluoro-3-phenoxyphenyl)-1,3-butadiene.

15. The process for the preparation of a 1,4-diaryl-2-fluoro-2-butene compound of the structural formula III

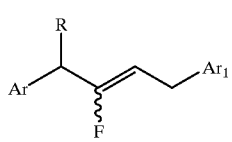

(III)

wherein
R is hydrogen, $C_1$–$C_4$alkyl, $C_1$–$C_4$haloalkyl, $C_3$–$C_6$cycloalkyl or $C_3$–$C_6$halocycloalkyl;
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups,
1- or 2-naphthyl optionally substituted with any combination of from one to three halogen, $C_1$–$C_4$alkyl, $C_1$–$C_4$haloalkyl $C_1$–$C_4$alkoxy or $C_1$–$C_4$haloalkoxy groups, or
a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and
Ar$_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, which process comprises:

(a) reacting a 1,4-diaryl-2-fluoro-1-buten-3-ol compound of the structural formula I

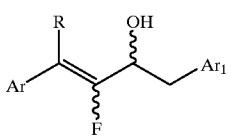

(I)

wherein Ar, $Ar_1$ and R are as described above with a sulfonyl chloride or sulfonic acid anhydride compound and a base to form a 1,4-diaryl-2-fluoro-1,3-butadiene compound of the structural formula II

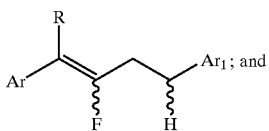

(II)

(b) reacting the 1,4-diaryl-2-fluoro-1,3-butadiene compound with: (1) an alkaline earth metal in the presence of a protic solvent, or (2) an alkali metal in the presence of an aprotic solvent.

16. The process according to claim 15 wherein the sulfonyl chloride is selected from the group consisting of phenylsulfonyl chloride, a substituted phenylsulfonyl chloride, a $C_1$–$C_6$alkylsulfonyl chloride and a $C_1$–$C_6$haloalkylsulfonyl chloride; and the sulfonic acid anhydride is selected from the group consisting of phenylsulfonic acid anhydride, a substituted phenylsulfonic acid anhydride, a $C_1$–$C_6$alkylsulfonic acid anhydride and a $C_1$–$C_6$haloalkylsulfonic acid anhydride.

17. The process according to claim 15 wherein the base is selected from the group consisting of an alkali metal hydride, an alkaline earth metal hydride, an alkali metal $C_1$–$C_6$alkoxide, a $C_1$–$C_6$alkyllithium and a lithium dialkylamide.

18. The process according to claim 15 wherein the 1,4-diaryl-2-fluoro-1-buten-3-ol compound is reacted with the sulfonyl chloride or sulfonic acid anhydride compound and the base in the presence of a solvent.

19. The process according to claim 18 wherein the solvent is selected from the group consisting of an ether, a carboxylic acid amide, a dialkyl sulfoxide, a nitrile, an aromatic hydrocarbon and a halogenated aromatic hydrocarbon and mixtures thereof.

20. The process according to claim 15 wherein the 1,4-diaryl-2-fluoro-1-buten-3-ol compound is reacted with the sulfonyl chloride or sulfonic acid anhydride compound and the base at a temperature ranging from about −78° C. to about 120° C.

21. The process according to claim 15 wherein the 1,4-diaryl-2-fluoro-1,3-butadiene compound is reacted with the alkaline earth metal in the presence of the protic solvent.

22. The process according to claim 21 wherein the alkaline earth metal is magnesium.

23. The process according to claim 21 wherein the protic solvent is a $C_1$–$C_6$alcohol.

24. The process according to claim 15 wherein
R is $C_1$–$C_4$alkyl, $C_1$–$C_4$haloalkyl, $C_3$–$C_6$cycloalkyl or $C_3$–$C_6$halocycloalkyl;
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and
$Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or
3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

25. The process according to claim 24 wherein
R is isopropyl or cyclopropyl;
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and
$Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

26. The process according to claim 15 for the preparation of a compound selected from the group consisting of
1-[1-(p-chlorophenyl)-2-fluoro-4-(4-fluoro-2-phenoxyphenyl)-2-butenyl]cyclopropane and
1-[1-(α,α,α-trifluoro-p-tolyl)-2-fluoro-4-(4-fluoro-3-phenoxyphenyl)-2-butenyl]cyclopropane.

27. A process for the preparation of a 1,4-diaryl-2-fluoro-1-buten-3-ol compound of the structural formula I

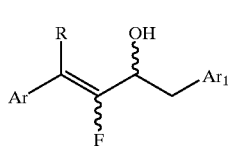

(I)

wherein
R is hydrogen, $C_1$–$C_4$alkyl, $C_1$–$C_4$haloalkyl, $C_3$–$C_6$cycloalkyl or $C_3$–$C_6$halocycloalkyl;
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups,
1- or 2-naphthyl optionally substituted with any combination of from one to three halogen, $C_1$–$C_4$alkyl, $C_1$–$C_4$haloalkyl $C_1$–$C_4$alkoxy or $C_1$–$C_4$haloalkoxy groups, or
a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and
$Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, which process comprises:

(a) reacting an arylmethanebromide compound of the structural formula IV

Ar$_1$CH$_2$Br          (IV)

wherein Ar$_1$ is as described hereinabove with a lithium $C_1$–$C_6$alkyltellurolate compound to form an intermediate compound of the structural formula V

Ar$_1$CH$_2$TeLi;          (V)

(b) reacting the formula V intermediate compound with a $C_1$–$C_6$alkyllithium compound to form an intermediate compound of the structural formula VI

Ar$_1$CH$_2$Li; and          (VI)

(c) reacting the formula VI intermediate compound with a 3-aryl-2-fluoropropenal compound of the structural formula VII

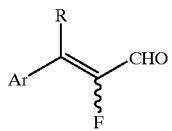

(VII)

wherein R and Ar are as hereinbefore defined.

28. The process according to claim 27 wherein the arylmethanebromide compound is reacted with the lithium $C_1$–$C_6$alkyltellurolate compound in the presence of a solvent to form the formula V intermediate compound, reacting the formula V intermediate compound in situ with the $C_1$–$C_6$alkyllithium compound to form the formula VI intermediate compound, and reacting the formula VI intermediate compound in situ with the 3-aryl-2-fluoropropenal compound.

29. The process according to claim 28 wherein the solvent is an ether.

30. The process according to claim 27 wherein

R is $C_1$–$C_4$alkyl, $C_1$–$C_4$haloalkyl, $C_3$–$C_6$cycloalkyl or $C_3$–$C_6$halocycloalkyl;

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and Ar$_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups, 3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or 3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

31. The process according to claim 30 wherein

R is isopropyl or cyclopropyl;

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and Ar$_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

32. The process according to claim 27 for the preparation of a compound selected from the group consisting of 1-(p-chlorophenyl)-1-cyclopropyl-2-fluoro-4-(4-fluoro-3-phenoxyphenyl)-1-buten-3-ol and 1-(α,α,α-trifluoro-p-tolyl)-1-cyclopropyl-2-fluoro-4-(4-fluoro-3-phenoxyphenyl)-1-buten-3-ol.

* * * * *